United States Patent [19]

Fuisz

[11] Patent Number: 5,196,199
[45] Date of Patent: Mar. 23, 1993

[54] HYDROPHILIC FORM OF PERFLUORO COMPOUNDS AND METHOD OF MANUFACTURE

[75] Inventor: Richard C. Fuisz, Washington, D.C.

[73] Assignee: Fuisz Technologies Ltd., Chantilly, Va.

[21] Appl. No.: 627,693

[22] Filed: Dec. 14, 1990

[51] Int. Cl.$^5$ .................... A61K 47/26; A61K 31/02; A61K 31/025; A61K 9/10

[52] U.S. Cl. ........................ 424/401; 424/484; 424/400; 514/832; 514/844; 514/873

[58] Field of Search ............... 424/401, 484; 514/832

[56] References Cited

U.S. PATENT DOCUMENTS

| 4,486,417 | 12/1984 | Sugimoto et al. | 514/53 |
|---|---|---|---|
| 4,873,085 | 10/1989 | Fuisz | 424/440 |
| 4,900,824 | 2/1990 | Dandliker et al. | 544/185 |
| 4,987,154 | 1/1991 | Long | 514/772 |
| 4,997,856 | 3/1991 | Fuisz | 424/426 |
| 5,028,632 | 7/1991 | Fuisz | 424/410 |

FOREIGN PATENT DOCUMENTS

| 0307087 | 8/1988 | European Pat. Off. |
| 2940184 | 10/1979 | Fed. Rep. of Germany |
| 8908459 | 3/1989 | PCT Int'l Appl. |
| 9006969 | 11/1989 | PCT Int'l Appl. |

Primary Examiner—Thurman K. Page
Assistant Examiner—E. J. Webman
Attorney, Agent, or Firm—Hoffmann & Baron

[57] ABSTRACT

Perfluoro derivatives of dimethyladamantane; tributylamine; dihexylether, 1-bromooctane; and tetradecahydrophenanthrene, for example, are rendered dispersable colloidally in water or other polar media without the aid of an emulsifying agent by melt spinning a mixture of the compound with a sugar. Thus, a family of new colloidal perfluoro compounds are produced.

24 Claims, No Drawings

HYDROPHILIC FORM OF PERFLUORO COMPOUNDS AND METHOD OF MANUFACTURE

BACKGROUND OF THE INVENTION

The present invention relates to hydrophilic substances containing perfluoro compounds and to methods of making emulsions containing perfluoro compounds.

In U.S. Pat. No. 4,855,326, issued Aug. 8, 1989 various substances having pharmacological properties were combined with a sugar and spun into fibers to produce a readily water-soluble product. The various examples enumerated in the patent all involved the use of water soluble medicaments and were directed to enhancing the solubility rate of the different substances. The patent describes methods for combining a medicament with any one or more of the water soluble melt spinnable sugars and spinning the combination to produce a readily soluble floss form of the medicament. The disclosure of such patent is incorporated herein by reference.

In co-pending application Ser. No. 07/283,742, filed Dec. 13, 1988, now U.S. Pat. No. 5,011,532, issued Apr. 30, 1991, the disclosure deals with oleaginous substances such as vegetable oil, baby oil, olive oil, margarine, lanolin, cocoa butter, and the like, and how their lack of affinity for water is altered by mixing the oleaginous substance with sugar and melt spinning the mixture in a cotton candy spinning machine or the equivalent. As so modified the products disperse autogenously in water forming a colloidal or pseudo-colloidal dispersion. Such modification enabled such widely disparate procedures as: (a) incorporating shortening oil in a cake mix containing flour but no egg to which water is added to produce a batter; and (b) producing a confection or medicated lozenge by dehydrating the dispersion and allowing the melted residue to solidify. The aforementioned application discloses that any oleaginous substance that can be mixed with a melt-spinnable sugar, when spun in a cotton candy spinning machine, produces a product which, when added to water or has water added to it, forms, virtually autogenously, a uniform dispersion having all the appearances of a colloidal dispersion. The disclosure of such application is incorporated herein by reference.

Other disclosures dealing with spinning substances with one or more sugars will be found in U.S. Pat. No. 4,873,085, issued Oct. 10, 1989, and in co-pending applications, Ser. Nos.: 07/325,643; 07/392,427; and 07/444,045; filed, respectively, Mar. 20, 1989; Aug. 10, 1989; and Nov. 30, 1989, now, respectively, U.S. Pat. Nos. 5,034,421; 5,028,632; and 4,997,856.

In application Ser. No. 07/325,643 it is explained that a spun product from a combination of a saccharide and a hydrophobic ingredient is hydrophilic with low concentrations of such ingredient but becomes increasingly hydrophobic as the concentration of the hydrophobic ingredient is increased, although the end product nevertheless acts hydrophilically when the water temperature is elevated. Beeswax is disclosed in the −643 application as being a moderating agent. As described therein, pure white pharmaceutical grade beeswax, a substance that is essentially hydrophobic, was mixed with sucrose and spun, producing an excellent floss which floated when added to normal room temperature water, but immediately dispersed with the appearance of being colloidal when added to water at about 180° F. (82.2° C.).

In the *Kirk-Othmer Encyclopedia of Chemical Technology*, 3rd ed., Suppl. Vol.-Alcohol Fuels to Toxicology, published by John Wiley & Sons, Copr. 1984, there appears, on pp. 159–171, an article entitled "Blood-Replacement Preparations" by Robert Geyer of Harvard University. The article deals with liquid perfluoro compounds which have been investigated for biomedical application. These nonpolar materials dissolve appreciable quantities of gases such as oxygen and carbon dioxide. The article lists 18 different compounds in a table on page 162 which compounds are identified as suitable for blood-replacement preparations. Among the compounds mentioned are: the perfluoro derivatives of dimethyladamantane, formula $C_{12}F_{20}$; tributylamine, formula $C_{12}F_{27}N$; dihexyl ether, formula $C_{12}F_{26}O$; and l-bromooctane, formula $C_8F_{17}Br$. All of the mentioned perfluoro compounds are colorless and odorless liquid organic compounds in which all hydrogens have been replaced with fluorine. They are essentially insoluble in water and other polar liquids. To provide a perfusion liquid the perfluoro compound has to be emulsified and this has required an emulsifying agent. The emulsifying agents must be strictly nontoxic for biomedical use. Frequently used emulsifying agenta are phospholipids such as egg-yolk phospholipids.

A proprietary product, "Pluronic F-68" produced by BASF Wyandotte Corp., is mentioned in the above article, and stated to be the most frequently used surfactant for blood-replacement preparations. However, the article states that the purified form of the surfactant must be stored at −25° C. or lower, preferably under nitrogen. The restriction on utility should be self-evident.

Use of the egg-yolk phospholipids has encountered problems in that experiments have uncovered a high rate of adverse human reaction to the phospholipids. Thus, prior to the present invention it has not been possible to produce a satisfactory in vivo perfusion liquid suitable for transfusion which is based on a perfluoro compound.

SUMMARY OF THE PRESENT INVENTION

It is, therefore, an object of the present invention to provide a mass of spun fibers containing a perfluoro compound but no emulsifying agent which mass of fibers when added to water disperses therein without the aid of an emulsifying agent to form a colloidal or pseudo-colloidal dispersion.

Other objects of the present invention are to provide an in vivo perfusion liquid containing a perfluoro compound in colloidal or pseudo-colloidal dispersion throughout a dispersing medium but without the presence of an emulsifying agent, and a method for producing such an in vivo perfusion liquid.

Another object of the present invention is to provide a hydrophilic form of a perfluoro compound which disperses readily in an aqueous medium to form a colloidal dispersion which can be incorporated economically and efficiently in conventional carrier agents for topical application.

Still further objects will occur to those skilled in the subject art after reading the following detailed description.

In accordance with one aspect of the present invention there is provided a perfusion product containing a perfluoro compound in colloidal or pseudo-colloidal dispersion throughout an aqueous dispersing medium free from any emulsifying agent.

In accordance with another aspect of the present invention there is provided a method for producing a perfusion product containing a perfluoro compound, comprising in combination the steps of producing a mass of spun fibers bearing a perfluoro compound by melt spinning a composition containing said perfluoro compound and a carrier agent, and dispersing said mass of fibers colloidally or pseudo-colloidally throughout an aqueous medium without employing an emulsifying agent.

In accordance with a further aspect of the present invention there is provided a mass of spun fibers consisting essentially of one or more sugars where the sugars are capable of being spun into fibers that are readily water-soluble, and a perfluoro compound that in its separate state is essentially insoluble in water and other polar liquids, said compound being distributed on or incorporated in the fibers of said mass such that said mass of fibers when added to water will disperse therein to form a colloidal or pseudo-colloidal dispersion.

The invention will be better understood after reading the following detailed description of the presently preferred embodiments thereof.

DETAILED DESCRIPTION OF THE PRESENTLY PREFERRED EMBODIMENTS

Typical of the discovery that has given rise to the present invention is that perfluoro compounds of the type and general character identified above can be mixed with a melt-spinnable sugar and thereafter spun in a cotton candy spinning machine to produce a product which, when added to water or has water added to it, forms, with a minimum or no agitation, a uniform dispersion having all the appearances of a colloidal dispersion. The invention can best be described and understood from a consideration of a number of examples.

For the following examples the floss spinning machine used was: Econo Floss Model 3017 manufactured by Gold Medal Products Co. of Cincinnati, Ohio. Unless otherwise stated, reference to sucrose in the examples is to "Domino" granulated sugar. Unless otherwise indicated, the temperature of the grid in the spinning machine was estimated to be at about 180° F. (82.2° C.) or somewhat higher while operating at a speed of about 3800 R.P.M. Under static conditions, assuming that the grid is stationary and out of contact with the saccharide, the grid temperature was estimated to be at about 500° F. (260° C.).

EXAMPLE I

One part by volume perfluorooctylbromide marketed by Alliance Pharmaceutical Corp., of San Diego, Calif. under the trademark "Imagent GI" was mixed with three parts by volume sucrose. It was mixed with a spoon in a glass vessel for about 5 minutes. The mixture was then spun using the floss spinning machine. A quantity of floss was produced. When some of this floss was added to a quantity of water at room temperature, the floss immediately dispersed in the water producing a mild to moderate Tyndall effect characteristic of a colloidal dispersion. Examination by microscope at a magnification of about 1200X reveals complete colloidal dispersion with the suspended particles averaging about 2 microns or less.

The "Imagent GI" material is supplied as a clear liquid which is intended to be taken orally undiluted prior to an NMR examination of the G.I. tract. Alliance Pharmaceutical also has for limited experimental use a colloidal dispersion form of perfluorooctylbromide intended for intravenous application. This form consists of equal quantities of perfluorooctylbromide and distilled water with sufficient egg yolk phospholipid to cause a complete dispersion. But, as explained previously, the egg yolk phospholipid causes adverse systemic reactions limiting the use of such product.

By contrast, the colloidal dispersion that is produced from the floss prepared in the present example, if dispersed in distilled water, can be given intravenously with none of the heretofore involved risks of an adverse reaction otherwise associated with the presence of the phospholipid.

Another name for this perfluoro compound is perfluoro 1-bromooctane having the formula, $C_8F_{17}Br$, and known by the abbreviation, FOB.

EXAMPLE II

Example I was repeated substituting for the sucrose an equal quantity of dextrose obtained from Sigma Chemical Co. of St. Louis, Mo. The results were essentially the same.

EXAMPLE III

The following compounds were obtained under generic labeling:

| Perfluoro derivative of | abbreviation | Formula |
| --- | --- | --- |
| dimethyladamantane | FDMA | $C_{12}F_{20}$ |
| tributylamine | FC-43 | $C_{12}F_{27}N$ |
| dihexyl ether | FHE | $C_{12}F_{26}O$ |

Each of the above compounds was mixed with sucrose in the same ratio as in Example I and spun into a floss with the same result. That is, an otherwise immiscible perfluoro compound was rendered miscible in water by spinning with sucrose.

The perfluoro compounds involved in the examples set forth above are representative of the entire class of such compounds identified in the above-mentioned article by Robert Geyer. All of the other perfluoro compounds identified in said article should spin with sucrose or dextrose in the same manner as described in Examples I, II and III hereof.

EXAMPLE IV 10 cc. of perfluoro (tetradecahydrophenanthrene) $C_{14}F_{24}$, from PCR Inc. of Gainesville, Fla., was added to 150 gm. of sucrose which was then mixed thoroughly. The resultant mixture was spun using the floss spinning machine identified above to produce a nice floss.

Next, 10 gm. of the floss was dispersed in 10 gm. of distilled water by stirring with a pipette. Then 5 drops of the liquid mixture were placed on a glass slide over which was placed a coverglass. Optical examination of the sample on the slide was accomplished using an Olympus Bh2 microscope. Particles were observed ranging in size from 0.2 microns to 2 microns. r

EXAMPLE V

Example IV was repeated using the perfluorooctylbromide of Example I instead of the perfluoro (tetradecahydrophenanthrene). Similar particle sizes were obtained in the dispersions.

From the foregoing it should be appreciated that any of the mentioned perfluoro compounds can be spun with a saccharide (sugar) to produce a floss which when added to distilled water can safely be administered intravenously. However, the colloidal dispersions produced from perfluoro compounds in the manner discussed above can also be incorporated in sundry media such as emollients, cosmetic creams and lotions for topical application where the perfluoro compound can release oxygen to the skin. For lanolin or oil based cosmetics or topical medicaments conventional homogenization techniques can be used, while for water based substances the dispersions can be added directly without any additional emulsifying agents or homogenization.

Having described the present invention with reference to the presently preferred embodiments thereof, it will be apparent to those skilled in the subject art that various changes and modifications can be incorporated without departing from the true spirit of the invention as defined in the appended claims.

What is claimed is:

1. A perfusion product containing a combination of a perfluoro compound and a sugar, said combination spun into a mass of fibers, wherein said product is water-dispersible, and such that when said product is added to an aqueous medium free from any emulsifying agent a colloidal dispersion is formed.

2. A perfusion produce according to claim 1, wherein said perfluoro compound is selected from the group consisting of perfluoro derivatives of dimethyladamantane, tributylamine, dihexyl ether, 1-bromooctane, tetradecahydrophenanthrene, and combinations thereof.

3. A method for producing a perfusion product containing a perfluoro compound, comprising in combination the steps of providing a mass of spun fibers bearing a perfluoro compound by melt spinning a composition containing said perfluoro compound and a sugar that can be spun into a product that is readily water-soluble, and dispersing said mass of spun fibers colloidally throughout an aqueous medium without employing an emulsifying agent.

4. A method according to claim 3, wherein said sugar is combined with said perfluoro compound to provide said composition as an intermediate product, and said intermediate product is converted to said mass of spun fibers by said melt spinning.

5. A method according to claim 4, wherein said sugar is selected from the group consisting of maltose, fructose, sorbitol, dextrose, mannitol, sucrose, lactose, and combinations thereof.

6. A method according to claim 4, wherein said sugar is sucrose.

7. A method according to claim 4, wherein said sugar is dextrose.

8. A method according to claim 3, wherein said aqueous medium is distilled water.

9. A method according to claim 8, wherein said sugar is combined with said perfluoro compound to provide said composition as an intermediate product, and said intermediate product is converted to said mass of spun fibers by said melt spinning.

10. A method according to claim 9, wherein said sugar is selected from the group consisting of maltose, fructose, sorbitol, dextrose, mannitol, sucrose, lactose, and combinations thereof.

11. A method according to claim 9, wherein said sugar is sucrose.

12. A method according to claim 9, wherein said sugar is dextrose.

13. A method for producing a form of a perfluoro compound which form is dispersible colloidally in an aqueous medium without the aid of an emulsifying agent, said method comprising the steps of producing a mass of spun fibers bearing said perfluoro compound by melt spinning a composition containing said perfluoro compound and a sugar.

14. A method according to claim 13, wherein said composition is provided by mixing said perfluoro compound with a melt spinnable compatible water soluble sugar.

15. A method according to claim 14, wherein said sugar is selected from the group consisting of maltose, fructose, sorbitol, dextrose, mannitol, sucrose, lactose, and combinations thereof.

16. A method according to claim 14, wherein said sugar is sucrose.

17. A method according to claim 14, wherein said sugar is dextrose.

18. A mass of spun fibers consisting essentially of one or more sugars wherein the sugars can be spun into fibers that are readily water-soluble, and a perfluoro compound that in its separate state is essentially insoluble in water and other polar liquids, said compound being distributed on or incorporated in the fibers of said mass in the absence of an emulsifying agent such that said mass of fibers when added to water without an emulsifying agent will disperse therein to form a colloidal or pseudo-colloidal dispersion.

19. A colloidally dispersible mass of spun fibers including a mixture of spinnable sugars and a perfluoro compound which is devoid of an emulsifying agent and colloidally dispersible in an aqueous medium without the aid of an emulsifying agent.

20. A colloidally dispersible mass of spun fibers including a mixture of spinnable sugars and a perfluoro compound according to claim 19 which is the result of melt spinning a mixture of the perfluoro compound and a sugar.

21. A colloidally dispersible mass of spun fibers including a mixture of spinnable sugars and a perfluoro compound according to claim 20, wherein said perfluoro compound is selected from the group consisting of perfluoro derivatives of dimethyladamantane, tributylamine, dihexyl ether, 1-bromooctane, tetradecahydrophenanthrene, and combinations thereof.

22. A product comprising a medium for a topical application, said medium having dispersed therethrough an aqueous dispersion free of any emulsifying agent, wherein said aqueous dispersion contains a mass of spun fibers dispersed throughout said aqueous dispersion and wherein said spun fibers include a mixture of spinnable sugars and a perfluoro compound.

23. A product according to claim 22, wherein said medium for topical application comprises an oil based cosmetic composition.

24. A product according to claim 22, wherein said medium for topical application comprises a water based cosmetic composition.

* * * * *